(12) United States Patent  
Moreau-Gaudry et al.

(10) Patent No.: US 8,534,131 B2  
(45) Date of Patent: Sep. 17, 2013

(54) SURGICAL INTERVENTION DEVICE COMPRISING AN INSTRUMENT LIKELY TO DEFORM

(75) Inventors: Alexandre Moreau-Gaudry, Meylan (FR); Agnes Bonvilain, Myans (FR)

(73) Assignee: Universite Joseph Fourier—Grenoble 1, St. Martin d'Heres (FR)

( * ) Notice: Subject to any disclaimer, the term of this patent is extended or adjusted under 35 U.S.C. 154(b) by 229 days.

(21) Appl. No.: 13/059,141

(22) PCT Filed: Aug. 14, 2009

(86) PCT No.: PCT/EP2009/060561  
§ 371 (c)(1),  
(2), (4) Date: Feb. 15, 2011

(87) PCT Pub. No.: WO2010/020591  
PCT Pub. Date: Feb. 25, 2010

(65) Prior Publication Data  
US 2011/0137330 A1  Jun. 9, 2011

(30) Foreign Application Priority Data  
Aug. 19, 2008  (FR) ...................................... 08 55617

(51) Int. Cl.  
*G01B 5/30*  (2006.01)

(52) U.S. Cl.  
USPC ............................................. 73/760; 73/768

(58) Field of Classification Search  
USPC ................... 73/760, 768, 775, 777  
See application file for complete search history.

(56) References Cited

U.S. PATENT DOCUMENTS

| | | |
|---|---|---|
| 5,405,337 A | 4/1995 | Maynard |
| 5,830,144 A | 11/1998 | Vesely |
| 6,447,478 B1 | 9/2002 | Maynard |

(Continued)

FOREIGN PATENT DOCUMENTS

| | | |
|---|---|---|
| DE | 44 08 730 | 9/1995 |
| EP | 1 857 038 | 11/2007 |

(Continued)

OTHER PUBLICATIONS

Liwei Lin, et al. "A Micro Strain Gauge with Mechanical Amplifier" Journal of microelectromechanical systems, vol. 6, N°. 4, Dec. 1997, pp. 313-321.

(Continued)

*Primary Examiner* — Max Noori  
(74) *Attorney, Agent, or Firm* — Harness, Dickey & Pierce, P.L.C.

(57) ABSTRACT

The disclosure relates to a surgical intervention device, including a surgical instrument capable of passing through human or animal tissue and a system comprising so-called "passive" components capable of measuring deformation or a local strain of the instrument and/or so-called "active" components capable of imposing a local strain on the instrument, the system comprising at least two series of passive components arranged at the surface of the instrument so as to establish a biunivocal relation between the position of the instrument or the position of the distal end of the instrument and all the data originating from the series, and, where required, at least two series of active components arranged at the surface of the instrument. The disclosure also relates to a process for determining the position of the distal end of a surgical instrument capable of passing through human or animal tissue.

19 Claims, 5 Drawing Sheets

(56) References Cited

U.S. PATENT DOCUMENTS

| | | | |
|---|---|---|---|
| 6,679,836 | B2 | 1/2004 | Couvillon, Jr. |
| 6,997,870 | B2 | 2/2006 | Couvillon, Jr. |
| 7,169,155 | B2 | 1/2007 | Chu et al. |
| 7,211,048 | B1* | 5/2007 | Najafi et ............... 600/508 |
| 7,261,686 | B2 | 8/2007 | Couvillon, Jr. |
| 7,892,166 | B2* | 2/2011 | Long ........................ 600/144 |
| 7,927,327 | B2* | 4/2011 | Lu et al. ..................... 606/1 |
| 8,299,679 | B2* | 10/2012 | Chommeloux et al. .. 310/313 R |
| 2005/0059883 | A1 | 3/2005 | Peterson |
| 2006/0111618 | A1 | 5/2006 | Couvillon, Jr. |
| 2007/0016067 | A1 | 1/2007 | Webster et al. |
| 2007/0032734 | A1* | 2/2007 | Najafi et al. ............... 600/513 |
| 2007/0270649 | A1 | 11/2007 | Long |
| 2010/0160930 | A1* | 6/2010 | Green et al. ............... 606/130 |
| 2010/0256504 | A1 | 10/2010 | Moreau-Gaudry et al. |

FOREIGN PATENT DOCUMENTS

| | | |
|---|---|---|
| WO | WO 94/19051 | 9/1994 |
| WO | WO 99/60267 | 11/1999 |
| WO | WO 03/094759 | 11/2003 |
| WO | WO 2009/027277 | 3/2009 |
| WO | WO 2009/027278 | 3/2009 |
| WO | WO 2009/027279 | 3/2009 |

OTHER PUBLICATIONS

Ishihara et al., "Micro Mechatronics and Micro Actuators" IEEE ASME Transactions on Mechatronics, vol. 1, N° 1, Mar. 2006, pp. 68-79.

Kaiguo Yan et al., "'Smart' Needle for Percutaneous Surgery Influential Factor Investigation" Proceedings of the 29th Annual International Conference of the IEEE EMBS, Cité Internationale, Lyon, France, Aug. 23-26, 2007, 4 pages.

Roger G. Gilbertson et al., "A survey of micro-actuator technologies for future spacecraft missions" The Journal of the British Interplanetary Society, vol. 49, pp. 129-138, 1996.

Thorbjörn Ebefors, et al., "A robust micro conveyer realized by arrayed polyimide joint actuators" J. Micromech. Microeng. 10 (2000), pp. 337-349.

Thorbjörn Ebefors, et al., "New small radius joints based on thermal shrinkage of polyimide in V-grooves for robust self-assembly 3D microstructures" J. Micromech. Microeng. 8 (1998), pp. 188-194.

Thorbjörn Ebefors, et al., "A walking silicon micro-robot" The 10th Int Conference on Solid-State Sensors and Actuators (Transducers'99), Sendai, Japan, Jun. 7-10, 1999, pp. 1202-1205.

Vinutha Kallem, et al., "Image-guided Control of Flexible Bevel-Tip Needles" 2007 IEEE International Conference on Robotics and Automation Roma, Italy, Apr. 10-14, 2007.

Marseea H. Howard, et al. "An Electronic Device for Needle Placement during Sonographically Guided Percutaneous Intervention" Radiology Mar. 2001; vol. 218, No. 3, pp. 905-911.

Robert J. Webster III, et al., "Toward Active Cannulas: Miniature Snake-Like Surgical Robots" Proceedings of the 2006 IEEE/RSJ International Conference on Intelligent Robots and Systems Oct. 9-15, 2006, Beijing, China, pp. 2857-2863.

\* cited by examiner

SURGICAL INTERVENTION DEVICE COMPRISING AN INSTRUMENT LIKELY TO DEFORM

CROSS-REFERENCE TO RELATED APPLICATIONS

This application is a National Phase Entry of International Application No. PCT/EP2009/060561, filed on Aug. 14, 2009, which claims priority to French Patent Application Serial No. 0855617, filed on Aug. 19, 2008, both of which are incorporated by reference herein.

FIELD OF THE INVENTION

The present invention relates to a surgical intervention device comprising a surgical instrument capable of passing through human or animal tissue likely to deform and a system for determining the position of the instrument and the position of its distal end, that is, the end intended to intervene on a determined target, relative to its proximal end, that is, the end attached to an intermediate support manipulable by the practitioner.

BACKGROUND

In the scope of percutaneous medical procedures for diagnostic or therapeutic purposes, guided or not by imaging, an instrument likely to deform is introduced through the skin for reach a previously identified target. Different types of instruments are commonly used in daily medical practice for such interventions, such as for example probes, catheter guides, catheters, fibroscopes, probes, rods, and needles. For ease of execution of these procedures localisation and navigation tools have been developed for displaying, in real time and in a virtual environment representative of reality, the target, the position of the model of the instrument as well as its future trajectory.

The help given to the clinician by these novel tools allows him to guide the instrument to the target more precisely, resulting in a drop in morbidity. Yet, current localisation and navigation tools make the hypothesis of the indeformability of the instrument used, a hypothesis often not verified in current practice due to interactions of the instrument with human or animal tissue. In fact, interaction of the deformable instrument with human or animal tissue (soft tissue, hard osseous obstacle or other) is the origin of deformations of the instrument which can cause the interventional medical procedure to fail.

For example, interaction of the bevel of a straight flexible needle with tissue during deep biopsy can generate deflection responsible for failure of the puncture biopsy, with potential lesions of adjacent tissue (nerves, arteries). Inversely, the target can be mobilised following interaction of the instrument with human soft tissue originating in a failed procedure. Faced with these difficulties, it accordingly appears necessary to enrich the virtual environments of navigation representative of reality, by giving them the capacity to follow the exact position of the whole of the deformable instrument and deformed so as to specify in real time the relative positions of the instrument, of its distal end and of the target.

It would also be preferable to locally restrict the deformable instrument to correct its trajectory in light of reaching the target and improve the quality of the medical procedure. So, document U.S. Patent Publication No. 2005/0059883 describes the positioning of strain gauges on the proximal part of a flexible instrument, with a view to detecting the deflection of the instrument. The value of this deflection is taken into account by the navigation system to indicate the position of the distal end of the instrument. However, the type of device described takes into account only simple deformation (deflection) and not complex deformations (multiple curvatures), though more representative of reality, due to the unevenness of forces applied along the instrument. In addition, determining the position of the end of the instrument from data of proximal deformation presupposes a certain "regularity" of deformation of the instrument, in particular able to be incompatible with the very nature of the instrument (multiple curvatures). Finally, the proposed device is passive, that is, it does not modify the trajectory of the tool.

U.S. Pat. No. 5,830,144 provides for enclosing the tool in an elastomer or rigid sheath with a view to follow its position in real time. The sheath contains piezoelectric elements supplying a signal for detection of the position of the instrument by an echographic or electromagnetic localisation system. However, deformations of the instrument are not determined intrinsically at the instrument but extrinsically: the sheath, an element external to the instrument, must in effect be visible in real time by the localisation system to be able to identify its deformations, from which those of the instrument contained in the sheath are deduced. The necessity for visibility of the sheath within the tissue human constitutes a significant limitation of the device presented.

In addition, the quality of the junction between the sheath and the instrument appears to be essential to be able to deduce the position of the instrument from the position of the sheath. In fact, an instrument intended to pass through tissue naturally has a particularly smooth surface, but this surface state cannot ensure correct adherence of an attached element such as a sheath. Displacement of the sensors relative to the instrument can accordingly occur, causing imprecision in measuring, with potentially dramatic consequences for making gestures requiring much precision.

Document U.S. Pat. No. 7,261,686 proposes the use of a catheter guide comprising a plurality of actuators arranged over its length and a control unit of these actuators receiving information from strain gauges for example. In the proposed device, the catheter guide is introduced into a hollow anatomical structure the purpose of which is to deform to allow the catheter to move in the preferred direction. Once positioned, it can be "anchored" by modification of its rigidity. Highly useful for placing the catheter, this device requires control of direct imaging of the part within the organism. In addition, it permits only indirect guiding, by way of the guide, of the instrument (the catheter), and not direct navigation of the instrument inserted into the guide.

U.S. Patent Publication No. 2007/0016067 presents a robotised device for guiding a bevelled needle to a target by the combination of translation and rotation movements of the latter. This technique needs modelling of the mechanical tissular properties as well as detection of the needle and of its end on imaging acquired periodically. The use of a kinematic and not holonomic model associated with a careful combination of translation and rotation parameters of the needle helps correct the trajectory of the needle. However, using this method requires the capability of detecting the needle and its end, an easy process for X-ray imaging (fluoroscopic images) but which could be much more difficult for ultrasound imaging devices, for example (identification of the end of a needle also constitutes one of the difficulties of punctures guided under echographic imaging). In addition, for 2D echographic imaging this implicitly involves having positioning of the needle in the image acquisition plane.

In "'Smart' Needle for Percutaneous Surgery: Influential Factor Investigation", of Yan et al. (Proceedings of the 29th Annual international Conference of the IEEE EMBS, Aug. 23-26, 2007), the authors are interested in knowledge of the deflection of a needle and of its mobilisation by the use of piezoelectric actuators. In the approach presented, the end of the needle is detected by use of an electromagnetic sensor arranged at the end of the needle. In this case, it is however necessary to have direct display of the needle to act appropriately. The current limitations of electromagnetic localisation systems should also be pointed out.

A first aim of the invention is to propose a device capable of taking into account complex deformations, and a fortiori simple deformations, of an instrument intended to pass through human or animal tissue. Such a device should be able to know, at any time and using a localisation or navigation system, the position of the distal end of the instrument relative to its proximal part, and/or the position of the whole instrument potentially deformed relative to its proximal part. Another aim of the invention is to locally restrict the deformable instrument in light of facilitating its being guided to the target.

SUMMARY

In keeping with the invention, a surgical intervention device is proposed, comprising a surgical instrument capable of passing through human or animal tissue and a system comprising so-called "passive" components capable of measuring deformation or a local strain of the instrument and/or so-called "active" components capable of imposing a local strain on the instrument, said system comprising at least two series of passive components arranged at the surface of the instrument so as to set up a biunivocal relation between the position of the instrument or the position of the distal end of the instrument and all the data originating from said series, and, where required, at least two series of active components arranged at the surface of the instrument. According to a first embodiment, said system comprises at least two series of passive components arranged according to two generatrices of the surface of the instrument belonging to two distinct planes passing through the axis of the instrument, defining a referential in a plane orthogonal to the axis of the instrument. Said passive components advantageously comprise electromechanical microsystems, such as piezoelectric sensors and/or strain gauges. Preferably, the passive components are incorporated into the surface of the instrument.

According to a particular embodiment, each series comprises a single passive component, which comprises a longitudinal conductive element, in the form of at least one coil, extending parallel to the axis of the instrument over substantially the entire length of the instrument. The instrument preferably has at least one deformable zone, such as a local decrease in thickness and/or articulation, and the passive components are arranged on said zone. According to another aspect, said system also comprises at least two series of active components arranged on at least one preferential deformation zone of the instrument. Said active components advantageously comprise electromechanical microsystems, such as thermal, piezoelectric, pneumatic, electromagnetic, and/or electrostatic actuators. Preferably, the active components are incorporated into the surface of the instrument.

According to a particularly advantageous embodiment, said system comprises at least two series of passive components and two series of active components. For example, the passive components of each series are distributed substantially over the entire length of the surgical instrument and/or the active components are arranged on at least one preferential deformation zone of the distal part of the instrument. The device comprises preferably a coupling system of the passive and active components.

Another object relates to a process for determining the position of the distal end of a surgical instrument capable of passing through human or animal tissue, comprising the arrangement, at the surface of the instrument, of at least two series of so-called "passive" components capable of measuring deformation or a local strain of the instrument, and calibration in which a biunivocal relation is set up between all the data originating from each series of passive components and the position of the instrument or the position of the distal end of the instrument, and, where required, the arrangement, at the surface of the instrument, of at least two series of so-called "active" components capable of imposing a local strain on the instrument. Said process also comprises a localisation step of the target to be reached and of the distal end of the instrument. Another object of the invention relates finally to a production process of a surgical intervention device such as described hereinabove, comprising incorporation, on the surface of the instrument, of passive components and, where required, active components, by means of micro-production techniques.

BRIEF DESCRIPTION OF THE DRAWINGS

Other characteristics and advantages of the invention will emerge from the following detailed description in reference to the attached diagrams, in which.

DETAILED DESCRIPTION

The device comprises an instrument connected to a passive system capable of measuring deformations of the instrument and, optionally, an active system capable of applying deformations to the surgical instrument. The instrument to which the invention applies is an instrument capable of passing through tissue, as different to an instrument intended to follow anatomical ducts. It is not however perfectly rigid and is likely to deform. The instrument can be a needle, employed for example for puncturing, for a biopsy or for delivering at the level of an anatomical target a therapeutic substance (for example, an antibiotic, an anti-inflammatory). The instrument can also be a rod or the like.

The instrument in question has an elongated form, that is, its length is much greater than its diameter. The instrument will preferably have cylindrical contours. The instrument is typically made of metallic material, but can also be made of any biocompatible material and compatible with the use of passive and/or active components described hereinbelow.

A proximal end, or base, which is the end connected to the device allowing the practitioner to manipulate the instrument, and an opposite distal end, which is intended to reach the intended target are defined for this instrument. For easy penetration into tissue, the distal end is preferably pointed, for example in the form of a bevel. If this is an instrument intended for puncturing or delivery of a therapeutic substance (antibiotic, anti-inflammatory), it is hollow. So, in the case of a needle intended for punctures or deep biopsies, the outer diameter is of the order of 1 to 1.8 mm, the thickness of the wall is around 0.3 mm, the length is tens of cm (for example 17 cm). These descriptive elements are examples which naturally vary as a function of the depth of the target and of the nature of the tissue to be passed through to reach the target.

Figure 1:
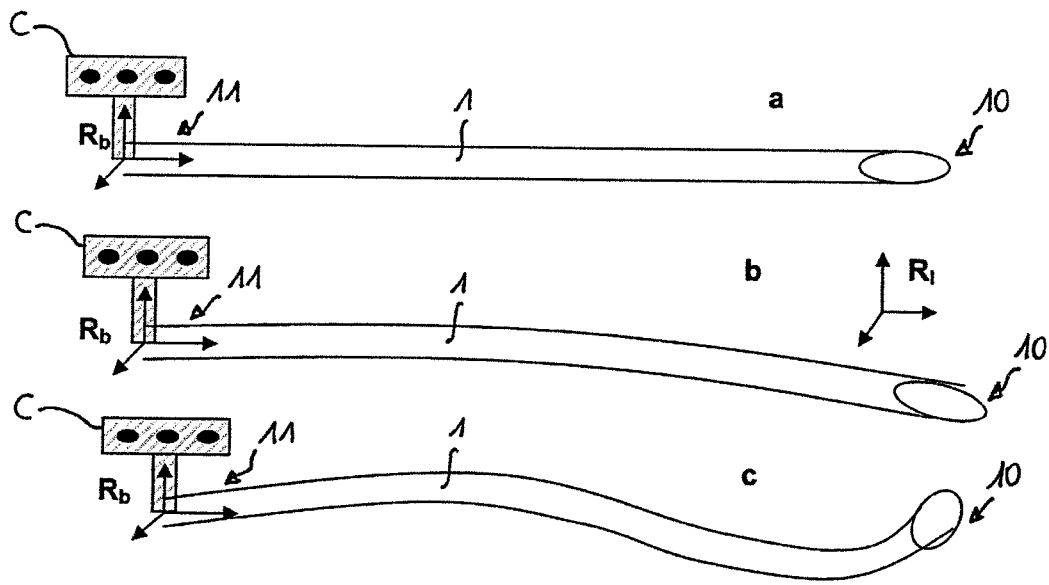
FIG. 1 illustrates different possible deformations of the instrument, and the referentials associated with the base of the instrument and the localiser.

FIG. 1 diagrammatically illustrates the instrument 1 in a non-deformed position (diagram a) and two deformed positions, one consisting of simple deformation or deflection (diagram b), the other complex deformation, with multiple curvatures (diagram c). The device according to the invention is designed so as to precisely restore information relative to these different types of deformations. The passive and active systems associated with the instrument will now be described.

Passive Components

The passive system is constituted by a mechanical system comprising passive components and by an electronic system capable of processing the information originating from the components. The passive components are components capable of measuring a strain or local deformation and transforming it into an electric signal (voltage, intensity . . . ) characteristic of this deformation. Each component is fixed on a region of small area (typically less than 10 mm$^2$) of the surface of the instrument, and locally measures deformation of the surface on which the component is fixed, or the strain exerted on this surface.

The passive components are connected according to at least two series. "Series" here means an entity whereof an electric signal representative of deformation of the instrument is measured. It is specified that in the present text "deformation" of the instrument must be understood as signifying deformation of the axis of the instrument.

If the series is constituted by a single passive component, the signals electric originating from of this single component are taken into account, which gives information on deformation or the local strain (at the site of this component); if the series is constituted by at least two carefully placed components, all the electric signals originating from the different components are taken into account, providing overall information on the deformation of the instrument. Since at least two distinct series of passive components are arranged on the instrument, taking into account all the electric signals originating from the different series of components determines all the local strains exerted on the instrument. The overall strain and accordingly the deformation and the position of the distal end of the instrument relative to its proximal end can be deduced therefrom.

Different types of passive components can be used, such as for example electromechanical microsystems (MEMS), and more particularly sensors based on piezoelectric materials, strain gauges and/or any other type of sensors. By way of example, the selected passive components are strain gauges, such as those marketed under the reference FLK-2-17 by the company Tokyo Sokki Kenkyujo, which are adapted specifically to measuring strains on cylinders.

Figure 2A:
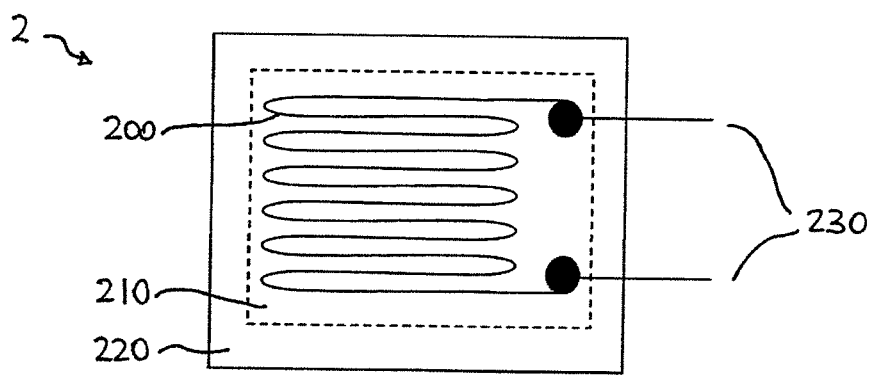
FIGS. 2A to 2C diagrammatically illustrate the structure and the operating principle of a strain gauge.
Figure 2B:
Figure 2C:
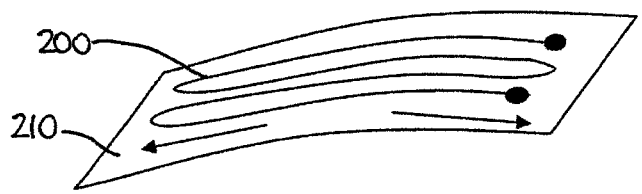

The structure and operating principle of these strain gauges are explained diagrammatically in FIGS. 2A to 2C. As is evident from FIG. 2A, the strain gauge 2 comprises a long conductive element 200 which is arranged in the form of coils on the trial body 210. In general, the conductor, not deformed, is characterised by its electrical resistance R and its length L. The trial body undergoes deformation at the origin of the deformation of the long conductor. During deformation of the conductor, its resistance variation $\Delta R$ is a function f of that of its length $\Delta L$: $\Delta R = f(\Delta L)$. The conductive element 200 is connected at each of its ends to connectors 230. The assembly is fixed on a support 220 which ensures linking between the deformable instrument and the trial body 210.

FIG. 2B illustrates initial deformation which tends to compress the trial body 210 and the element 200 (approaching arrows). In this case, the overall resistance of the gauge diminishes due to the shortening of the length of the conductive element. FIG. 2C illustrates inverse deformation which tends to tense the trial body 210 and the element 200 (arrows moving away). In this case, the overall resistance of the gauge increases due to the increase in length of the conductive element.

Because the strain gauges and the piezoelectric sensors are commercially available components, they will not be described in any further detail. The person skilled in the art can select the most appropriate components from catalogues of different manufacturers as a function of their sensitivity, their capacity to be fixed on the instrument, etc. It is of course possible to combine different types of passive components on the same instrument, as the electric signals received are compatible.

Arrangement of the Components on the Instrument

The components of the same series are carefully positioned on the surface of the instrument and connected to attain the aim of the invention. Their number and their disposition are selected by the person skilled in the art according to the possibilities of deformation of the instrument (for example, deflection or deformation with multiple curvatures) and the preferred aim.

In general, the possibilities of the instrument to deform are taken into account, especially due to the fact of its length and its diameter, and the components are positioned at strain concentration points, that is, those points of preferential deformation of the instrument. For this purpose, the person skilled in the art can produce a model of the instrument and simulate its deformation under the effect of strains predefined as a function of usage provided. To give reliable indications, this modelling must consider the environment of the instrument (nature of pierced tissues, interactions between tissues and the instrument . . . ).

The components of each series can be placed over the entire length of the instrument to avoid this step of determining sites of maximal concentration of strains, ensuring that all deformations are considered. So, if the instrument is likely to deform according to multiple curvatures (case of a long and fine needle), the components are distributed over substantially the entire length of the instrument so as to more finely measure local deformations from which overall deformation is deduced. The interval between two sensors is a function of the possibilities of deformation of the instrument and of the preferred precision.

Deformable zones can be defined on the instrument particularly advantageously in view of avoiding the modelling step of deformations of the instrument. For this purpose, local decreases in the thickness of the instrument can be created, for example, at the level of which the instrument will preferably flex. Alternatively, an articulated instrument can be used which will deform at the level of articulations.

The sites of preferential deformation of the instrument are imposed, irrespectively of the strains which are applied during piercing of tissue. In this case, the passive components are positioned on the imposed deformation zones. In this way and by way of example, for an instrument of which two preferential deformation zones have been identified (or imposed), the sensors will be positioned at the surface of these two zones so as to best consider local information contributed by these deformation zones, from which the overall position could be deduced. However, if the instrument is likely to deflect only in a certain direction (case of a short needle, for example), it can be sufficient to place the components in the region of the proximal end of the instrument.

In the case where the instrument has a cylindrical form, two series of components can be placed on two distinct generatrices of the surface of the instrument. These generatrices are selected both so that they take into account preferential deformations of the instrument, and also so that they maximise the information acquired by each series of components. Each generatrix defines a plane with the axis of the instrument not deformed. In a plane perpendicular to the axis of the instrument, the layout of the planes thus defined defines a referential and a system of coordinates.

Figure 3A:
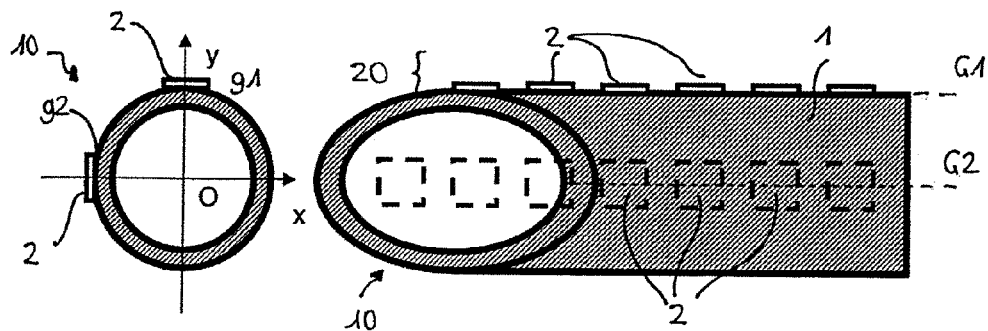
FIGS. 3A and 3B illustrate an example of arranging two series of passive components on a bevelled instrument, in a facing view and in side elevation, not deformed (FIG. 3A) and deformed (FIG. 3B)

FIG. 3A illustrates a disposition example of two series 20, 21 of passive components at the surface of the instrument 1. In this figure, the components have been arranged according to two generatrices G1, G2 belonging to two orthogonal planes. The layouts of these planes, visible in the left part of FIG. 3A, can define an orthogonal referential (O,x,y) of Cartesian or polar coordinates. The axis of the instrument not deformed accordingly has coordinates (0, 0) in this referential.

Figure 3B:
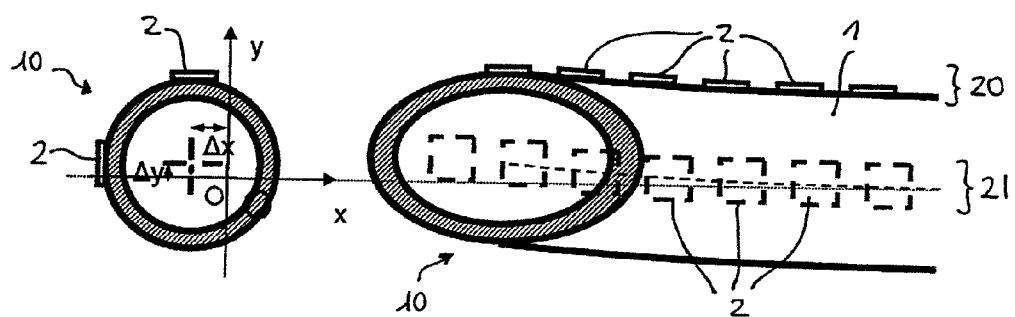

FIG. 3B illustrates the same instrument in the deformed state. The axis (here at the level of the distal end 10) of the instrument now has coordinates ($\Delta x$, $\Delta y$) in this same referential.

Also, when the distal end 10 of the instrument has a bevel; it is advantageous to take this into consideration in positioning the series of passive components. In fact, the bevel makes up a physical characteristic of the instrument, contributing to a certain direction of deformation during its insertion into human or animal tissue. As is evident from FIGS. 3A and 3B, the generatrix G2 has been selected corresponding to the point of the bevel. In the referential of FIG. 3A, this generatrix projects in a point g2 on the axis Ox. The generatrix G1 is selected so that the angle not oriented (g1,O,g2) is 90°, g1 being the orthogonal projection on the axis Oy of G1 in the referential previously identified.

Also, in this example, the components of the two series 20 and 21 belong two by two to a plane perpendicular to the axis of the instrument. Any other type of configuration can be selected without as such departing from the scope of the present invention. Therefore, by way of example, it is feasible to place the components according to one or more helicoidal curves at the surface of the instrument, or else randomly, provided that the data (typically, the potentials) originating from each series of components enable determination of a biunivocal relation with the position of the instrument relative to its base, and/or with the position of its distal end relative to its base.

It is also possible of consider the torsion of the instrument. In fact, according to the tissue passed through, a long and fine surgical instrument is also likely to deform torsionally along its axis in addition to "conventional" deformations. The device of the invention measures this deformation torsionally by having, in addition to the above passive components, which measure local deformations in planes locally containing the axis of the instrument, passive components arranged substantially orthogonally to the preceding ones so as to measure local deformations in planes substantially orthogonal to said axis of the instrument. Measurements originating from all the above passive components accordingly determine the position of the distal end of the instrument with even greater precision.

Fixing the Components

The passive components can be fixed on the instrument by any appropriate known to the person skilled in the art and compatible with the surgical use of the instrument. They can be for example adhered by means of specific adhesives developed by the makers of the components, preferably incorporated into housings made in the surface of the instrument so as not to exceed the surface of the instrument and not interfere with the tissues passed through to avoid any risk of relative displacement of the components vis-à-vis the instrument. However, according to a more preferred embodiment which will be described hereinbelow, the passive components are integrated into the wall of the instrument by means of microproduction techniques.

Connection of the Components and Electronic System

The individual information of each passive component can be processed either individually, or "integratively" or overall. In the first case, each component constitutes for itself a series and is connected to the electronic system which processes the information originating from each component. This system detects deformations of the instrument at each point where a sensor is positioned.

Figure 4:
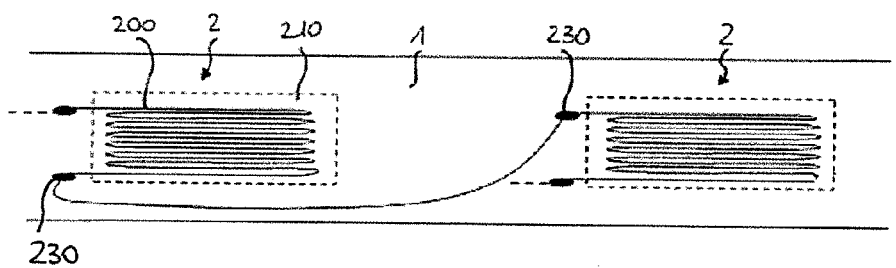
FIG. 4 illustrates the series connection of two passive components fixed on the surface of the instrument.

Within the scope of "integrative" processing of data, the components of the same series are connected in series, as illustrated in FIG. 4. Therefore, during the deformation of the instrument, the components within the same series are encouraged to deform, which modifies their respective resistances and consequently the overall resistance of the series. The variations in voltage induced at the terminals of each series of components reflect the elementary displacements of the instrument in each of the respective planes, orthogonal to the axis of the instrument such as defined previously.

After a calibration step, that is, following setting up of a univocal relation between deformations of the instrument and the electric data measured by the passive components, it is possible determine the position of the distal end of the instrument relative to its proximal end from knowledge of the voltage information. Accordingly, by way of illustration and with reference to the orthogonal referential defined by the conditions of FIGS. 3A and 3B, the displacements $\Delta x$ and $\Delta y$ of the distal end of the instrument in this orthogonal referential are deduced respectively from the information of potentials made by the series of components arranged respectively along the generatrices G1 and G2.

In addition, on the proviso of adapted density of components along the generatrices, it is also possible to deduce deformation of the whole instrument. For this purpose, each series of components is integrated within an adapted electronic circuit, allowing acquisition of the pertinent electric signals from which the preferred spatial information (deformation and/or position of the distal end of the instrument) are deduced in light of being, for example, taken into account in a navigation system.

Figure 5:
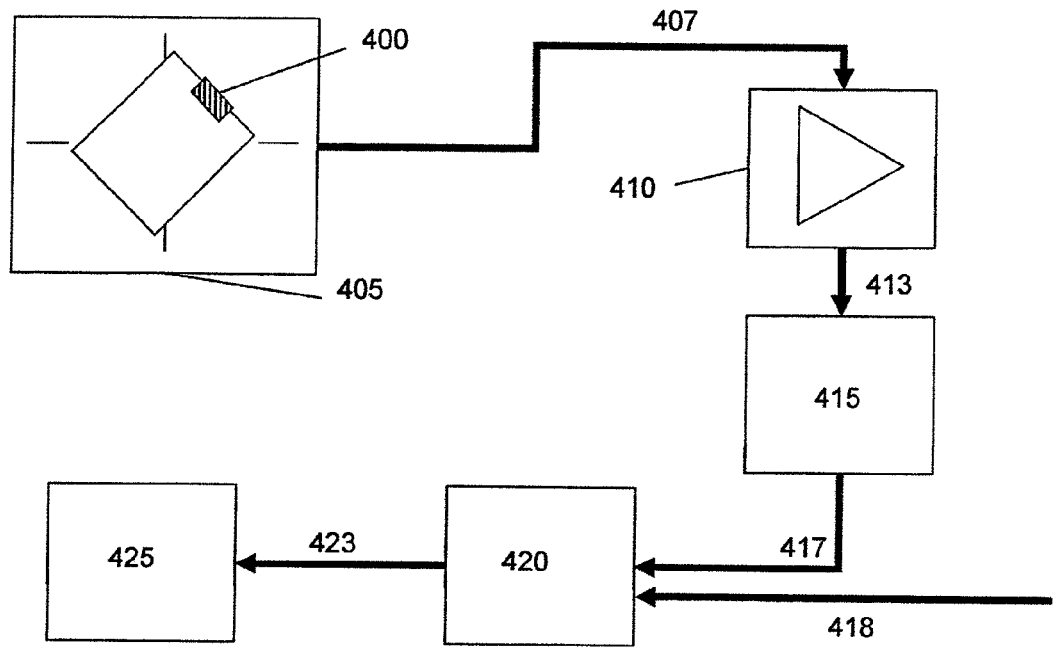
FIG. 5 is a diagram of an electronic device for processing information originating from the passive components.

Appropriate examples of electronic circuits are for example the TI XTR 106 circuit which is an instrumentation circuit provided for measuring by strain gauges. The diagram of FIG. 5 illustrates an example of an electronic circuit utilised for each series of components. The series 400 is integrated into a Wheatstone bridge 405 to reveal slight variations in resistance of the ensemble.

The output voltage 407 of the bridge is amplified by an amplifier 410 then transferred to a linearisation device 415 which linearises the output voltage if necessary. The output signal 417 is then injected within a microcontroller 420, the particular aim of which is to transform the signal according to standardised communication protocol interpretable by a computer. This signal 423 is processed in a computer 425 and is interpreted as a function of information coming from other peripherals, such as for example a linearised voltage signal 418 of another series of components, information of a navigation or imaging system, etc. Advantageously, the electronic system can have a so-called "offset" function for automatically or manually setting at zero the output voltage of each series of passive components when the instrument is not deformed.

Incorporation of Passive Components in the Instrument

According to a particularly advantageous aspect of the invention, the passive components are not elements connected to the instrument, but are incorporated into the surface of the latter via micro-production techniques. This avoids any risk of relative displacement of passive components relative to the instrument, which ensures the truly biunivocal character of the relation between the position of the instrument or of the distal end of the latter and the data originating from the passive components. This process typically involves techniques for depositing a conductive element on the surface of the instrument, then etching through a mask to give the conductive element the preferred form. Reference could be made here to the article by L. Lin et al., "A Micro Strain Gauge with Mechanical Amplifier", Journal of Microelectromechanical Systems, Vol. 6, No. 4, December 1997.

It is possible to incorporate the conductive element over the entire length of the instrument and according to different generatrices. In fact, at the surface of the instrument and according to the preferred angular distribution, the fineness and precision of micro-production techniques create a plurality of strain gauges each constituted by a conductive element arranged to form at least one coil. This distribution, in particular, improves the detection of deformations of the instrument.

Figure 6:
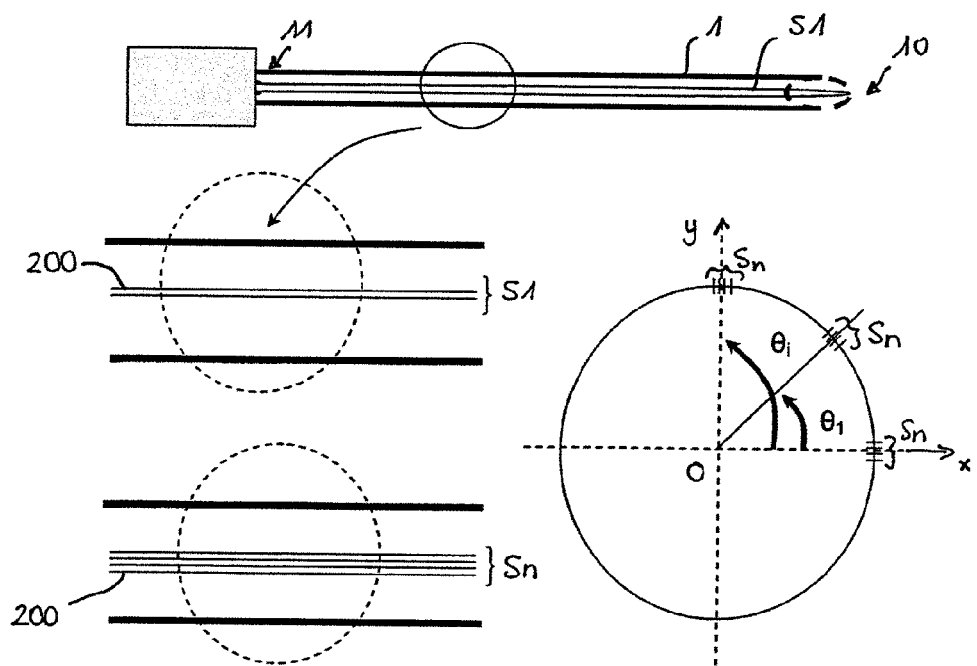
FIG. 6 illustrates a particular embodiment of the incorporation of passive components at the surface of the instrument.

FIG. 6 illustrates incorporation on the surface of the instrument 1 of a conductive element forming a single coil S1 (i.e. a single return journey of the conductor, of the base of the instrument at its end), arranged over the entire length of the instrument. Similarly, to boost detection quality, a conductive element Sn comprising a number n of longitudinal coils (going from the base of the instrument to its end) can be arranged over the entire length of the instrument. Finally, as illustrated on the right view of this figure, which is a sectional view of the instrument, several longitudinal conductive elements Sn can be distributed over the circumference, each being marked by its angle θ in the orthogonal system of polar coordinates mentioned hereinabove. In this case, each conductive element S1 or Sn is a passive component constituting a series in itself.

By way of illustration, in the case of deflection of the instrument (such as illustrated in FIG. 1b), the conductive element with maximal (and/or minimal) potential directly determines the angular direction of principal deformation and accordingly the preferential direction of displacement of the distal end of the instrument, to the resolution of the angular distribution. This configuration has the advantage of making etching of the different longitudinal elements easy by repetition of a plurality of identical steps. At each step of micro-production, rotation can be made of the instrument according to its axis by an elementary angular pitch.

Figure 7:
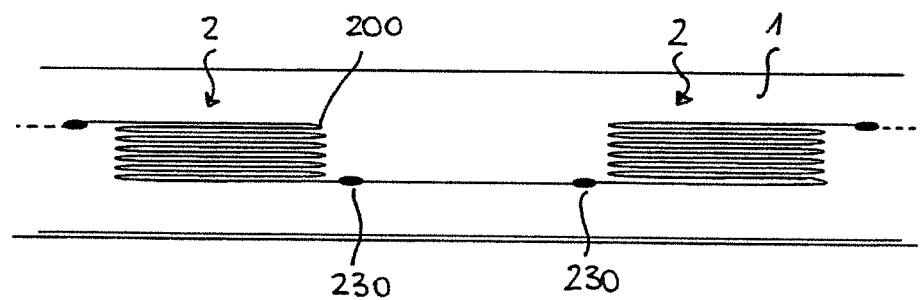
FIG. 7 illustrates the series connection of two passive components incorporated into the surface of the instrument.

Other longitudinal configurations and other angular distributions over all or part of the circumference of the instrument are of course feasible. As a variant, it is possible to incorporate not just an "integrative" system such as that of FIG. 6 but a series of elementary systems to measure local deformations then deduce therefrom an overall deformation. An example is illustrated in FIG. 7. The micro-production techniques actually develop a miniaturised and optimised system especially in terms of interfacing, which is often a weak point or even limiting of "macroscopic" systems due to its fragility and bulk. As is evident from FIG. 7, the micro-production techniques of the conductive element 200 actually place the gauges 2 in series on a generatrix with the connectors 230 of two consecutive gauges vis-à-vis each other. This constitutes a relative advantage to the connection of gauges such as illustrated in FIG. 4.

Active Components

In addition to the system for measuring deformations, the device can comprise a so-called "active" deformation system, the purpose of which is to apply at predefined points of the instrument strains for deforming it or on the contrary for preventing its deformation. This guides the distal end of the instrument to the target to be reached by taking focus off organs situated on its trajectory. This active system comprises a mechanical system and an electronic system.

The mechanical system comprises connecting so-called "active" components, situated on a region of small area of the surface of the instrument, and capable of applying strain generating deformation to this region. The active components can be based on different principles according to which the energy supply causes mechanical action. Electromechanical microsystems (MEMS) are feasible here, and more particularly piezoelectric, thermal, pneumatic, electromagnetic, electrostatic, etc. actuators.

Just as for the passive components described hereinabove, the active components are fixed on the instrument in housings provided for this purpose, or else they are preferably incorporated into the surface of the latter by micro-production techniques. They are distributed according to at least two series and are arranged at preferable deformation sites of the instrument. For example, the active components of each series are distributed according to two distinct generatrices of the surface of the instrument.

In the case of a piezoelectric actuator, application of voltage elongates the actuator in its housing, and accordingly applies compressive forces on the edges of this housing, causing stiffening or on the contrary curving of the instrument. The articles "Micro Mechatronics and Micro Actuators", Ishihara et al., IEEE/ASME Transactions on Mechatronics, Vol. 1, No. 1, March 2006 and "A Survey of Micro-Actuator Technologies for Future Spacecraft Missions" of Gilbertson et al., Journal of the British Interplanetary Society, Vol. 49, pp. 129-138, 1996, address panoramas of different utilisable actuation modes.

It is understood that the active components will be selected by the person skilled in the art as a function of their performance. Accordingly, in the category of piezoelectric actuators, multilayer actuators develop large forces but weak deflections, while bi-morphic or multi-morphic actuators engender strong deflections but weak forces.

Figure 8:
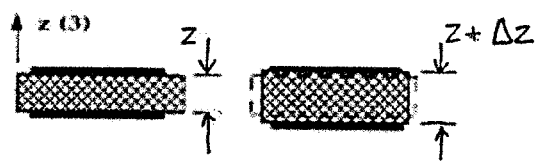
FIG. 8 diagrams a multilayer actuator which can be used as active component.
Figure 8:
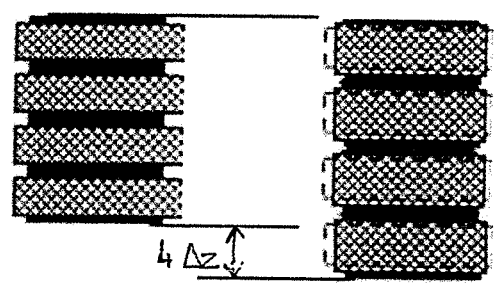

FIG. 8 illustrates a multilayer actuator constituted by a stack of circular elements. The electric load of an element makes it deform by increasing its thickness z by a value Δz and by reducing its surface. The thickness of a stack of circular elements undergoing the same load increases accordingly in proportion to the number of stacked elements, amplifying deformation. Also, the direct and inverse effects of piezoelectric materials can be used to determine deformations of the instrument and produce actuators, insofar as the component imposes sufficient deformation as actuator. According to another approach, the active components are thermal actuators arranged within micro-articulations based on polyimides, according to the concept presented in the articles of T. Ebefors et al., "New small-radius joints based on thermal shrinkage of polyimide in V-grooves for robust self-assembly 3D microstructures", Micromech. Microeng. 8 (1998) 188-194, "A walking silicon micro-robot", Transducers'99, Jun. 7-10 1999, pp 1202-1205, and "A robust micro conveyer realized by arrayed polyimide joint actuators", J. Micromech. Microeng. 10 (2000) 337-349.

Figure 9:
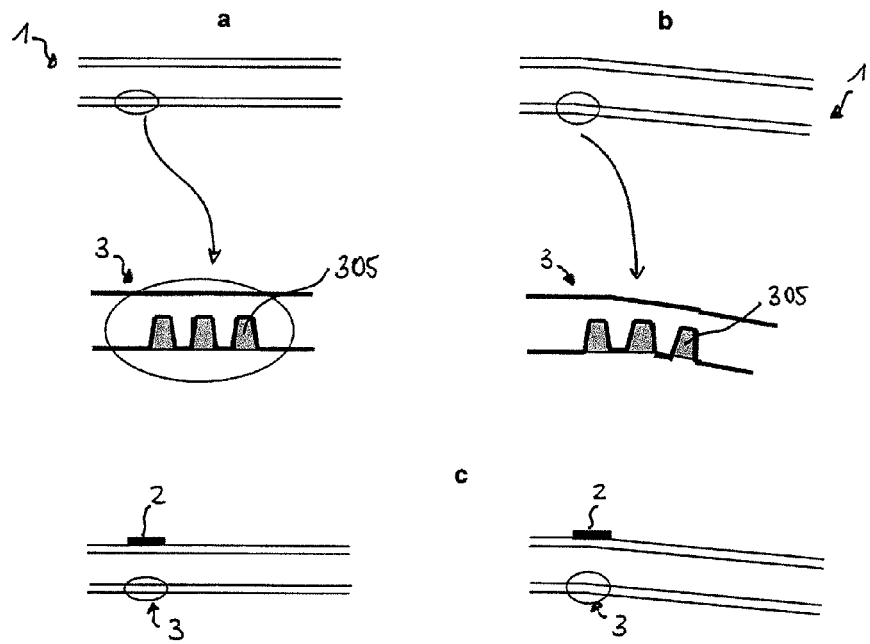
FIG. 9 illustrates the incorporation at the surface of the instrument of micro-articulations comprising thermal actuators.

FIG. 9 illustrates an example based on the use of thermal actuators 305 arranged in micro-articulations 3 based on polyimide. The case a corresponds to the situation where the system is inactive, the instrument 1 not being deformed. When the local temperature rises, the actuator 305 contracts, deforming the micro-articulation 3 and modifying the curvature of the instrument. This situation is illustrated in diagram b. The ensemble can be covered in an insulating sheath to guarantee the biomedical compatibility vis-à-vis these variations in temperature. This type of micro-articulation can be incorporated into the surface of the instrument by means of micro-production techniques. In the variant illustrated on the diagram c, passive components 2 are coupled to the active components 3.

Coupling the Active and Passive Systems

Figure 10:
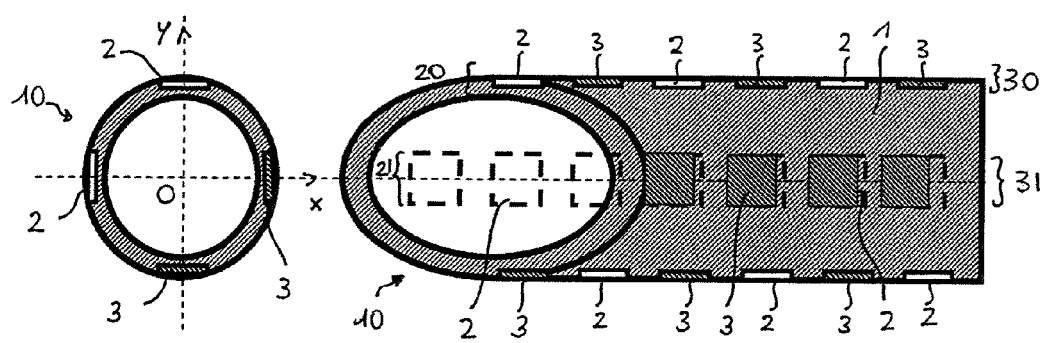
FIG. 10 illustrates a preferred embodiment of the invention, associating two series of passive components and two series of active components incorporated directly into the thickness of the instrument.

According to a non-limiting example, illustrated in FIG. 10, the instrument is preferably equipped with both passive components such described previously, such as strain gauges, and active components. In the example illustrated, the active and passive components are incorporated into the surface of the instrument by means of micro-production techniques mentioned hereinabove. Preferably, the series 30, 31 of active components 3 is arranged according to two generatrices diametrically opposite those of the two series 20, 21 of gauges 2.

As illustrated in FIG. 10, alternating at the level of each generatrix between passive and active components is naturally possible. A coupling system of the passive system and of the active system constitutes a dynamic device in which the strains to be applied to the instrument are adjusted in real time as a function of the preferred position, the result of the strains being evaluated by the passive system. Accordingly, as a function of the information originating from the gauges, the actuators correct the trajectory of the instrument in real time.

Figure 11:
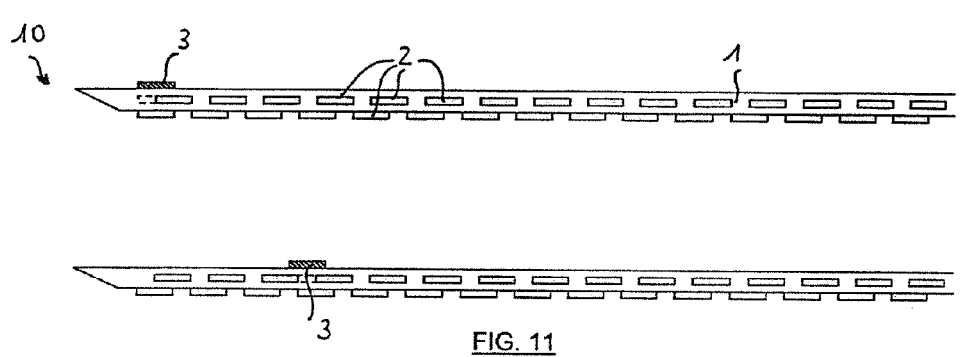
FIG. 11 illustrates an advantageous embodiment of the invention in which two series of passive components are incorporated over the entire length of the instrument and two series of active components are incorporated in the distal region of the distal end of the instrument.

This coupling can be carried out overall or at the level of the components. Accordingly, each passive component can be connected to an active component, as illustrated in FIGS. 9c and 10. It is not of course imperative for the series of passive components and of active components to have a similar arrangement. Accordingly, in reference to FIG. 11, a particularly advantageous embodiment consists of placing passive components over the entire length of the instrument, for example according to different generatrices, and positioning two series of active components in preferential deformation zones situated near the distal end of the instrument. This device mobilises the distal end of the instrument while knowing its overall deformation.

Calibration of the Device

Calibration means determining a correspondence (ideally biunivocal) between the information acquired by way of the passive components positioned on the instrument or the control information of deformations exerted by the active components positioned on the instrument, and the spatial information of the deformed instrument in a referential linked rigidly to the instrument (this, irrespectively of the deformations of the acceptable space of deformation of the instrument). In reference to FIG. 1, a rigid body C is fixed at the proximal end 11 (or base) of the instrument 1. The instrument is also equipped with passive and/or active components described hereinabove.

A first conventional calibration procedure finds out, in the referential $R_l$ of the localiser, the position of the base 11 of the instrument and its associated referential $R_b$, irrespective of the deformations of the instrument. During deformation of the instrument, each series of passive components is a carrier of information integrating local deformations in the vicinity of each strain sensor. A second calibration procedure is necessary to determine the biunivocal correspondence between the information of potentials connected by the series of components and the position of the distal end 10 of the instrument relative to its base 11, that is in the referential $R_b$. For example, simple deformation of the instrument can be calibrated by shifting in one plane the distal end of the instrument, using a device (robotic or not) of micrometric mobilisation of the distal end of the instrument.

The distal end of the instrument can be mobilised by the micrometric device over the entire acceptable mobilisation space of the distal end of the instrument (typically, a square surface), or according to two perpendicular directions simultaneously or else successively. The modalities of calibration depend in particular on adopted geometric configurations for the different series of components positioned on the instrument. In fact, in the case where the series of passive components has been arranged define an orthogonal referential (such as presented in FIGS. 3A and 3B), it is not necessary to carry out calibration for all points of the mobilisation space.

Determining this biunivocal relation, for example according to two perpendicular directions of displacement (or even four, for improvement of the quality of this step) allows deducing, by interpolation, this relation for displacements in all directions. On completion of this calibration procedure, it is possible to know the position of the distal end of the instrument in the referential $R_b$ associated with the base during deformation of the instrument. The position of the referential $R_b$ being itself known in the referential $R_l$ of the localiser, the position of the end of the instrument is thus known in Rl.

When the components of N series are arranged randomly on the surface of the instrument, definition of a referential is more delicate and it becomes possible to determine a biunivocal relation between the positions of the distal end of the instrument and the values of the N-uplet. In the case of disposable instruments, calibration should be conducted for each instrument. In the case of an instrument in which the passive components have been incorporated by the abovementioned micro-production techniques, and are accordingly not likely to move after intervention and sterilisation, it can be that calibration remains valid during successive uses of the instrument.

Localisation System

Localisation systems commonly employed within the scope of navigated medical procedures, using infrared, magneto-optic techniques, etc. can be employed in association with the measuring and/or application system of deformations. These systems rest on the principle of triangulation which defines the position of a point in space from its display in three different incidences.

Imaging System

The device according to the invention can be utilised in relation to all imaging systems commonly used for display of targets and compatible with the components utilised. Preferably, imagings navigated in real time are used, such as echographic imaging, fluorescent video imaging, inter alia. At any moment, calibrated imaging knows, via search ("tracking") of the target displayed on the image, the position of the target in the referential of the localiser. Due to the device according to the invention, the position of the deformed instrument in its entirety is known in the referential of the localiser.

Simultaneous knowledge of the position of the target and of the deformed instrument in the same referential of the navigated environment accordingly knows the relative position of the deformed instrument and of its distal end relative to the target. It is important of specify that, contrary to numerous procedures of the prior art, it is not necessary to display the deformed instrument on the image showing the target. In fact, this display is deduced from information acquired by the sensors arranged along the instrument and from the knowledge of the position of the rigid referential linked to the instrument (rigid body rigidly linked to the base of the instrument) in the common referential.

When the surgical gesture is being made, strains can be exerted in real time on the instrument by means the active components described hereinabove, so as to best correct the trajectory of the instrument. The instrument can be imposed on to go in a straight line to the target, or else follow a planned trajectory compatible with the degrees of mobility and deformation of the instrument.

Optionally, the active components themselves are calibrated, that is, a relation between the potential imposed on a series of active components, and the position of the distal end of the instrument relative to its proximal end have been defined previously. In this case, the use of passive components is not indispensable to the extent where, knowing the position of the target and that of the proximal end of the instrument by means of the localisation system, the practitioner can impose the potential necessary for each of the series of active components to obtain the preferred position for the distal end of the instrument. However, it is also possible, when the active components are coupled to the passive components, to consider information originating from the passive components to determine in real time the potential to be applied to the active components with a view to acquire the preferred position of the distal end. The surgeon proceeds via measurement application iterations of strains.

The device according to the invention applies especially in robotic surgical intervention procedures. Accordingly, document WO03/094759 describes a robot for positioning and orienting an instrument during a minimally invasive intervention. This robot is actuated by the surgeon to impose a translation or a rotation on the instrument according to its axis.

Equipping the instrument with passive and/or active components according to the invention gives the surgeon an instrument "with a homing head". With such a tool, the surgeon imposes on the instrument its movements of translation and/or of rotation in the direction of the target, while the passive and active systems control the position of the distal end of the instrument relative to the target. Also, the device can be further enriched by sensors for evaluating the quality of the tissues (for example cmUT (acronym of the English term "Capacitive Micromachined Ultrasonic Transducers") and evaluation of the tissue quality, fibre optics and spectral analysis for tissue evaluation, etc.).

ADVANTAGES OF THE INVENTION

Calibrating the device gives direct knowledge of the position of the instrument and/or of its distal end from all the signals delivered by the series of passive sensors. The possibility of better taking into account the deformations of the instrument—or even of influencing them—improves the precision of percutaneous interventions using the instrument. The direct consequence of this is being able to decrease the number of attempts necessary for making these gestures and accordingly, more generally, their morbidities. It will also probably be possible to envisage making novel gestures, not made to date since they are not feasible with current tools due to risks inherent in their execution.

Improvement in the possibility of guiding these instruments allows deep procedures with instruments of smaller diameter (augmentation of diameter of the instrument is a mean of avoiding deformations of the latter) and accordingly less invasive. Also, the use of micro-production techniques incorporates passive components and/or active into the surface of the instrument, avoiding strains associated with fixing modes (adhesion, sheath . . . ) of conventional components, but also strains linked to the electronic footprint, having a tool truly compatible with the clinical practice. Finally, the device applies not only to puncture interventions or biopsy, but has applications in minimally invasive surgery.

By way of example, taking into account deformations of a probe equipped with the system forming the object of the invention during navigated orthopaedic intervention, would improve the quality of localisation of the probed zone. Within the scope of laparoscopic surgery, the instruments manipulated by and equipped with the system as developed would offer the possibility of navigating it "naturally" in a common referential.

The invention claimed is:

1. A surgical intervention device, comprising:
   a surgical instrument capable of passing through human or animal tissue; the surgical instrument including a needle or a rod;
   a system comprising "passive" components capable of measuring a deformation or a local strain of the instrument; and
   wherein the system comprises at least two series of passive components arranged at the surface of the instrument so as to set up a biunivocal relation between the position of the instrument or the position of the distal end of the instrument and all the data issuing from the series.

2. The device as claimed in claim 1, wherein the system further comprises at least two series of passive components arranged according to two generatrices of the surface of the instrument belonging to two distinct planes passing through the axis of the instrument, defining a referential in a plane orthogonal to the axis of the instrument.

3. The device as claimed in claim 2, wherein the passive components comprise electromechanical microsystems.

4. The device as claimed in claim 2, wherein the passive components are incorporated into the surface of the instrument.

5. The device as claimed in claim 4, wherein each series of passive components comprises a single passive component which comprises a conductive element in the form of at least one longitudinally wound coil, extending parallel to the axis of the instrument over substantially the entire length of the instrument.

6. The device as claimed in claim 1, wherein the instrument has at least one deformable zone, such as a decrease in local thickness, an articulation, or a combination of both, and the passive components are arranged on the zone.

7. The device as claimed in claim 1, wherein the system further comprises at least two series of "active" components capable of imposing a local strain on the instrument, arranged at the surface of the instrument.

8. A production process of a device as claimed in claim 1, comprising incorporating in the surface of the instrument passive components, by micro-production techniques.

9. The device as claimed in claim 7, wherein the system comprises at least two series of active components arranged on at least one preferential deformation zone of the instrument.

10. The device as claimed in claim 9, wherein the active components comprise electromechanical microsystems.

11. The device as claimed in claim 9, wherein the active components are incorporated into the surface of the instrument.

12. The device as claimed in claim 7, wherein the passive components of each series are distributed substantially over the entire length of the surgical instrument and the active components are arranged on at least one preferential deformation zone of the distal part of the instrument.

13. The device as claimed in claim 7, further comprising a coupling system of the passive and active components.

14. A process for determining the position of the distal end of a surgical instrument capable of passing through human or animal tissue, the surgical instrument consisting of a needle or a rod, the process comprising:
the arrangement, at the surface of the instrument, of at least two series of "passive" components capable of measuring deformation or a local strain of the instrument;
calibration in which a biunivocal relation is set up between all the data originating from each series of passive components and the position of the instrument or the position of the distal end of the instrument; and
where required, the arrangement at the surface of the instrument of at least two series of "active" components capable of imposing a local strain on the instrument.

15. The process as claimed in claim 14, further comprising a localisation step of the target to be reached and of the distal end of the instrument.

16. A production process as claimed in claim 15, wherein the device further comprises at least two series of "active" components capable of imposing a local strain on the instrument, arranged at the surface of the instrument, the process comprising incorporating the active components in the surface of the instrument by micro-production techniques.

17. A surgical intervention device, comprising:
a surgical instrument for percutaneous medical procedures presenting a circumferential surface and a distal end;
a system comprising passive components capable of measuring a deformation or a local strain of the surgical instrument; and
the system comprising at least a first series of passive components and a second series of passive components arranged about the circumferential surface of the surgical instrument to generate a biunivocal relation between a position of the surgical instrument or a position of the distal end of the surgical instrument and all data issuing from the first and second series.

18. The device as claimed in claim 17, wherein the distal end of the surgical instrument presents a bevel defining a point for puncturing human or animal tissue.

19. The device as claimed in claim 18, wherein the first and second series of passive components are arranged according to two generatrices of the circumferential surface belonging to two distinct planes passing through an axis of the surgical instrument and defining a referential in a plane orthogonal to the axis, the first series of passive components being radially aligned with the point of the bevel.

* * * * *